(12) United States Patent
Ogle

(10) Patent No.: US 6,503,458 B1
(45) Date of Patent: Jan. 7, 2003

(54) AIR PURIFIER

(76) Inventor: William D Ogle, 2105 Bella Coola Rd., Lake Waccaman, NC (US) 28450

( * ) Notice: Subject to any disclaimer, the term of this patent is extended or adjusted under 35 U.S.C. 154(b) by 0 days.

(21) Appl. No.: 09/531,809

(22) Filed: Mar. 21, 2000

(51) Int. Cl.[7] ................................. A62B 7/08
(52) U.S. Cl. ....................... 422/121; 422/120; 422/122; 422/186.07
(58) Field of Search ................ 422/120, 121, 422/122, 5, 186.07

(56) References Cited

U.S. PATENT DOCUMENTS

| | | | |
|---|---|---|---|
| 3,486,308 A | | 12/1969 | Burt |
| 3,757,495 A | * | 9/1973 | Sievers .................. 250/436 |
| 3,967,927 A | * | 7/1976 | Patterson ................ 250/432 R |
| 4,210,429 A | * | 7/1980 | Golstein .................. 422/121 |
| 4,244,710 A | * | 1/1981 | Burger .................... 422/121 |
| 4,794,301 A | | 12/1988 | Misono et al. |
| 5,171,060 A | | 12/1992 | Kaye |
| 5,230,720 A | | 7/1993 | Kendall |
| 5,330,722 A | * | 7/1994 | Pick et al. .............. 250/436 |
| 5,616,172 A | | 4/1997 | Tuckerman et al. |

* cited by examiner

Primary Examiner—Krisanne Thornton
(74) Attorney, Agent, or Firm—Michael I. Kroll

(57) ABSTRACT

A device for purifying air within a room. The device includes a housing having a plurality of air inlet ports and a plurality of air outlet ports. An ultraviolet ray generator is positioned within the housing along with a fan for drawing air into the housing through the air inlet ports. A passageway leading from the air inlet ports and encircling the ultraviolet ray generator to the air outlet ports provides a path for air drawn into the housing. The ultraviolet rays produced by the generator kill bacteria, germs and viruses in the air passing thereby through the passageway and the passageway maximizes a distance traveled by the air through the housing and thereby maximizing exposure of the air to the ultraviolet rays. The device also generates ozone for neutralizing undesirable odors, such as stale tobacco smoke and mildew in the air drawn into the housing. First and second filter elements are positioned on opposing sides of the passageway for trapping small particles within the air drawn through said air inlet ports. The second filter element may be scented for providing a desired scent to air passing therethrough. An aperture is located in the housing adjacent the ultraviolet ray tube and further includes a viewing lens positioned to cover the aperture and thereby allow a person to look safely therethrough to determine if the ultraviolet ray tube is operating.

1 Claim, 3 Drawing Sheets

AIR PURIFIER

BACKGROUND OF THE INVENTION

1. Field of the Invention

The present invention relates generally to air filters and, more specifically, to a device contained within a decorative structure for removing impurities from and freshening the surrounding air using a physical filter and ultraviolet light, wherein exposure of the air drawn into the structure to the ultraviolet light is maximized.

2. Description of the Prior Art

Numerous air filters/decorative display fixtures have been provided in prior art. For example, U.S. Pat. No. 3,967,927 to Patterson; U.S. Pat. No. 4,210,429 to Golstein; U.S. Pat. No. 5,171,060 to Kaye and U.S. Pat. No. 5,330,722 to Pick et al. all are illustrative of such prior art. While these units may be suitable for the particular purpose to which they address, they would not be as suitable for the purposes of the present invention as heretofore described.

U.S. Pat. No. 3,967,927

Inventor: Lawrence Patterson

Issued: Jul. 6, 1976

An ultraviolet lamp fixture for purifying the air within a room by means of passing the air over a plurality of hot cathode or other commercially available ultraviolet ray tubes. The tubes are mounted vertically within a decoratively covered, easily movable, pole-mounted housing having a motorized fan which moves air through an opening in the lower portion of the housing over the tubes for purification. The purified air stream is exhausted through the top portion of the housing and returned to the room. The interior of the housing has deflector vanes which function to create a turbulent air flow in the area of the tubes to insure that all of the air passing through the lamp fixture is purified by contacting the lamps. The lamp fixture is provided with means for filtering the circulating air. In an alternate embodiment, the air passes through a dehumidifier prior to passing by the tubes.

U.S. Pat. No. 4,210,429

Inventor: Jerome J. Goldstein

Issued: Jul. 1, 1980

A room air purifier for quietly removing irritating or harmful impurities from the air circulating within the room. The purifier removes from room air, particles down to 0.3 microns in size with 99.9% efficiency. The air purifier comprises a somewhat elongated upright housing having an easily-removable back, a two-speed blower that is preferably AC operated and disposed at the bottom of the housing, a pair of vertically disposed ultraviolet lamps and associated means for powering the lamps including push button switch means, and preferably three separate filters including a pre-filter disposed at the inlet of the blower, a highly efficient main filter element vertically stacked over the blower and lamps and a charcoal filter disposed over the main filter element. The blower sucks the air in the bottom of the purifier through the pre-filter and up adjacent to the lamps to the main filter element and charcoal filter, and from there the purified air passes to a top baffle cover where the air is exited in preferably four directions from the purifier.

U.S. Pat. No. 5,171,060

Inventor: Howard Kaye

Issued: Dec. 15, 1992

An ornament displaying article of furniture having a weight-bearing surface member and pedestal base has a supporting substantially cylindrical and preferably transparent column releasably connected to the weight-bearing surface member. The appearance of the column may be altered with an agglomeration or reflective fill material, such as marbles, which may be exchanged by detaching the column from the weight-bearing surface member. In a preferred embodiment a light source irradiates light reflective or light radiant material of the fill.

U.S. Pat. No. 5,330,722

Inventors: William E. Pick and Kerby F. Fannin

Issued: Jul. 19, 1994

A germicidal air purifier for trapping and destroying airborne microorganisms is disclosed. The air purifier includes an ultraviolet radiation source and a juxtaposed filter medium. One ultraviolet radiation source and filter medium is fixed and the other is displaceable, so that at least an upstream side of the filter medium is systematically exposed to germicidal levels of radiation. In a first preferred embodiment, a fixed ultraviolet lamp irradiates a cylindrical air filter which is rotated on its longitudinal axis in close proximity to the lamp, so that the upstream side of the filter is systematically irradiated. In a second preferred embodiment, a radiant lamp fixture is moved reciprocally across an upstream side of a planar filter, to systematically irradiate the filter. In a third preferred embodiment, a radiant lamp fixture is rotated about an axis which is orthogonal to its longitudinal midpoint, so that a circular area of a planar filter is irradiated. The advantage is that microorganisms trapped on the filters are exposed to a lethal dose of radiation and the air purifier is consistently effective at destroying a significant percentage of airborne microorganisms suspended in the air passed through the filter.

SUMMARY OF THE INVENTION

The present invention relates generally to air filters and, more specifically, to a device contained within a decorative structure for removing impurities from and freshening the surrounding air using a physical filter and ultraviolet light, wherein exposure of the air drawn into the structure to the ultraviolet light is maximized.

A primary object of the present invention is to provide an air purifier that will overcome the shortcomings of the prior art devices.

Another object of the present invention is to provide an air purifier which is able to disinfect the air in the surrounding atmosphere, particularly in a sick-bay, to reduce the spread of infectious disease.

An additional object of the present invention is to provide an air purifier which emits ozone, a powerful oxidizing agent, for neutralizing undesirable odors, such as stale tobacco smoke and mildew.

A still further object of the present invention is to provide an air purifier which will expose air drawn therein to ozone and ultraviolet rays for a maximum possible amount of time.

An even further object of the present invention is to provide an air purifier including a passageway extending therethrough and surrounding the source of ozone and ultraviolet light through which air entering the purifier will flow.

A yet further object of the present invention is to provide an air purifier including a filter positioned at the inlet port for further purifying the air.

A still further object of the present invention is to provide an air purifier including a component for drawing air into the air purifier at the input port.

A further object of the present invention is to provide an air purifier that is simple and easy to use.

A yet further object of the present invention is to provide an air purifier that is economical in cost to manufacture.

Further objects of the invention will appear as the description proceeds.

A device for purifying air within a room is disclosed by the present invention. The device includes a housing having a plurality of air inlet ports and a plurality of air outlet ports. An ultraviolet ray generator is positioned within the housing along with a fan for drawing air into the housing through the air inlet ports. A passageway leading from the air inlet ports and past the ultraviolet ray generator to the air outlet ports provides a path for air drawn into the housing. The ultraviolet rays produced by the generator kill bacteria, germs and viruses in the air passing thereby through the passageway. The passageway maximizes a distance traveled by the air through the housing thereby maximizing exposure of the air to the ultraviolet rays. The device also generates ozone for neutralizing undesirable odors, such as stale tobacco smoke and mildew in the air drawn into the housing. A first filter element is positioned on a side of the passageway for trapping small particles within the air drawn through the air inlet ports. A second filter element may be scented for providing a desired scent to air passing therethrough and positioned on a side of the passageway opposite the first filter element. An aperture is located in the housing adjacent the ultraviolet ray tube and further includes a viewing lens positioned to cover the aperture and thereby allow a person to look safely therethrough to determine if the ultraviolet ray tube is operating.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWINGS

Various other objects, features and attendant advantages of the present invention will become more fully appreciated as the same becomes better understood when considered in conjunction with the accompanying drawings, in which like reference characters designate the same or similar parts throughout the several views, and wherein.

LIST OF REFERENCE NUMERALS

Figure 1:
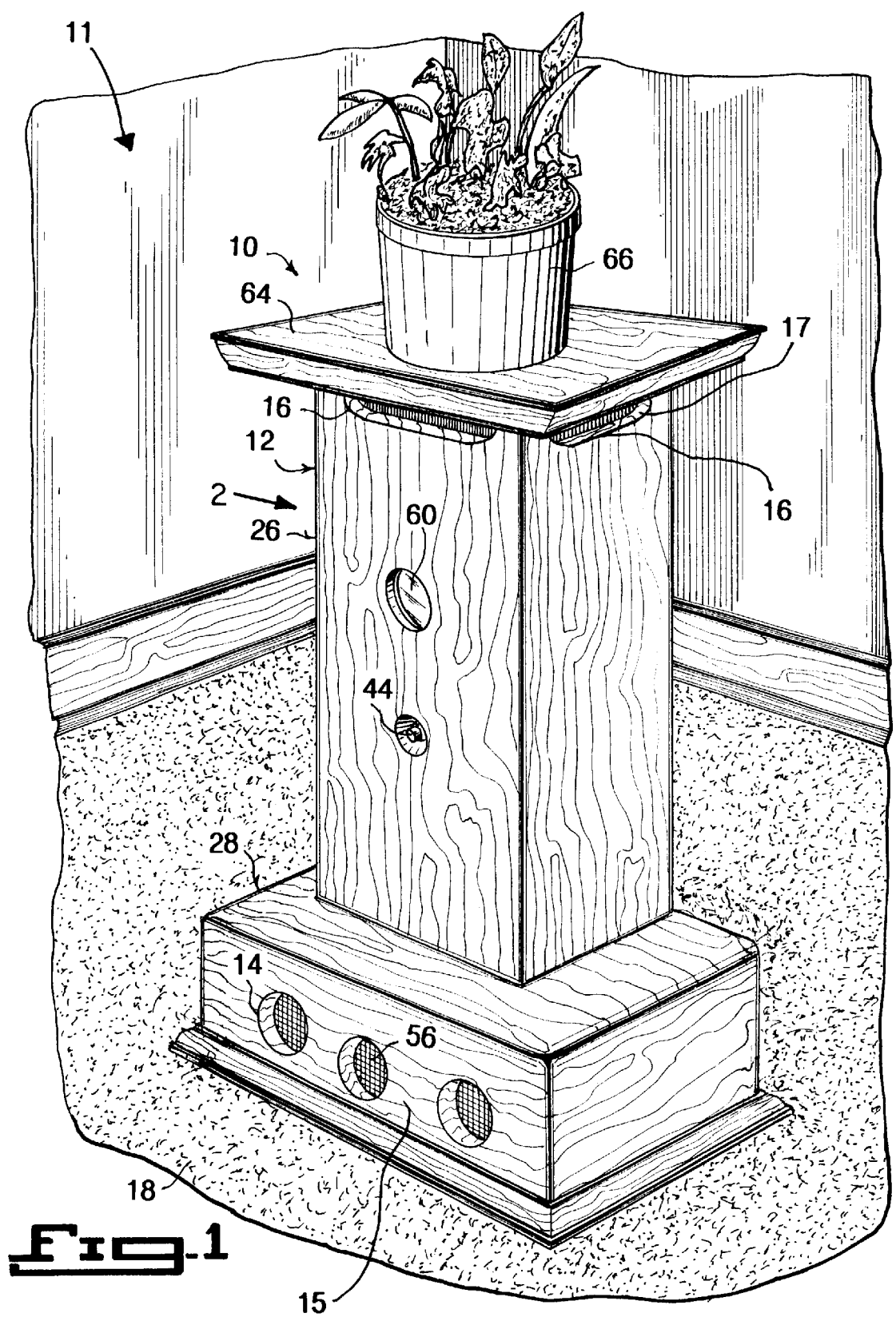
FIG. 1 is a perspective view of the instant invention being used as a flower stand in a room.

Turning now descriptively to the drawings, in which similar reference characters denote similar elements throughout the several views, the Figures illustrate the air purifier of the present invention. With regard to the reference numerals used, the following numbering is used throughout the various drawing figures.
10 air purifier of the present invention
11 room in which air purifier is positioned
12 housing of air purifier
14 air inlet port in housing
15 bottom side of housing
16 air outlet port in housing
17 top side of housing
18 floor
20 ultraviolet ray/ozone producing facility of air purifier
22 air drawing component of air purifier
24 small particle trapping element of air purifier
26 elongated enclosed cabinet of housing
28 hollow base member of housing
30 ultraviolet lamp assembly for ultraviolet ray/ozone producing facility
32 elongated chassis of ultraviolet lamp assembly
34 lamp holder of ultraviolet lamp assembly
36 ultraviolet ray tube of ultraviolet lamp assembly
38 electric circuit of ultraviolet lamp assembly
40 starter of ultraviolet lamp assembly
42 ballast of ultraviolet lamp assembly
44 switch of ultraviolet lamp assembly
46 plug of ultraviolet lamp assembly
48 electric cord of ultraviolet lamp assembly
50 blower for air drawing component
52 motorized fan of blower
54 high efficiency filter pad
56 polyester screen on air inlet port
58 aperture in elongated chassis
60 viewing lens in housing
62 removable back panel of housing
64 flat top plate of housing
66 flower pot on flat top plate
68 bottom access opening in housing
70 passageway
74 scented filter

DETAILED DESCRIPTION OF THE PREFERRED EMBODIMENT

Figure 2:
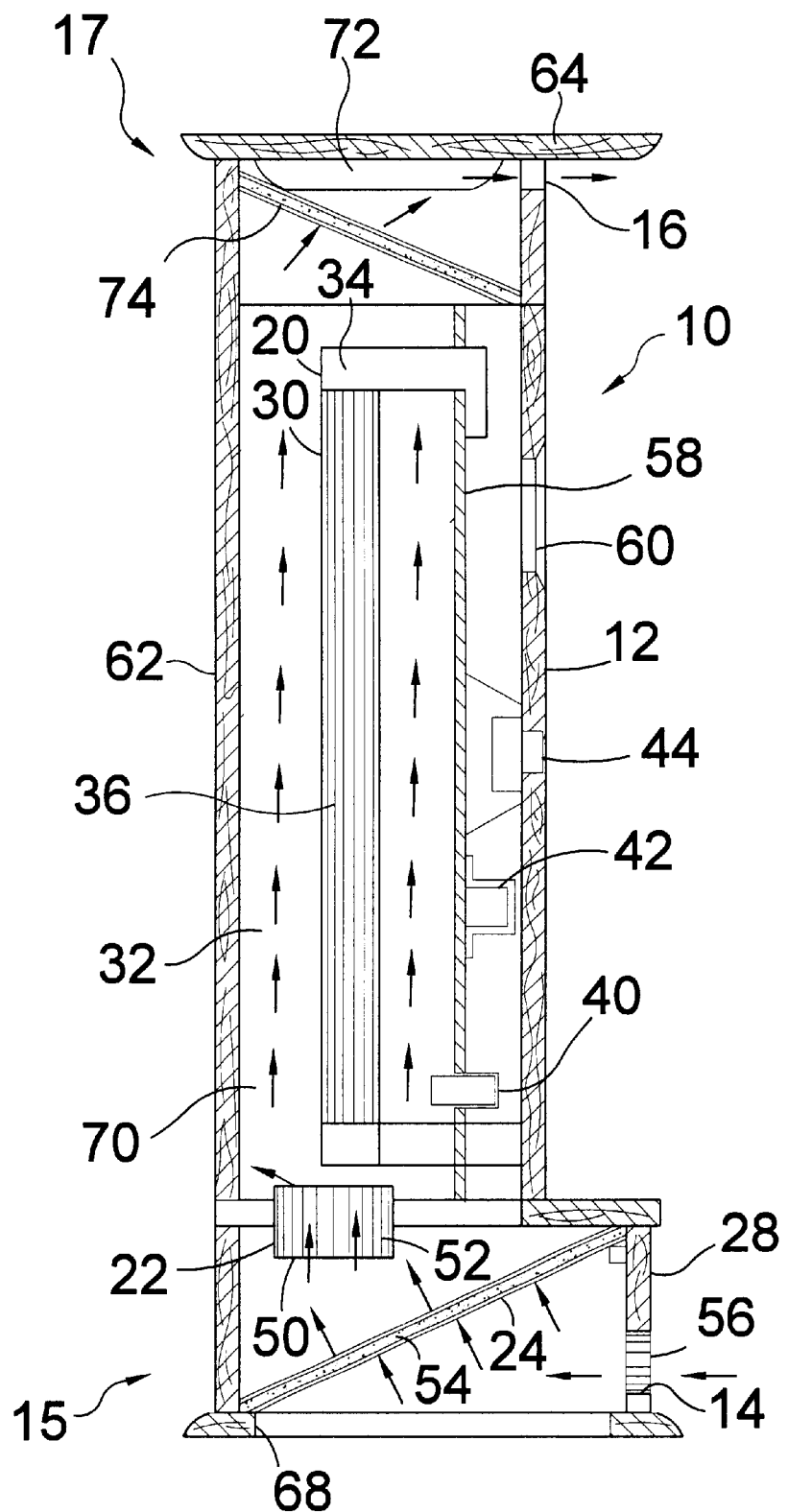
FIG. 2 is a side view of the instant invention per se taken in the direction of arrow 2 in FIG. 1, with parts broken away and in section.
Figure 3:
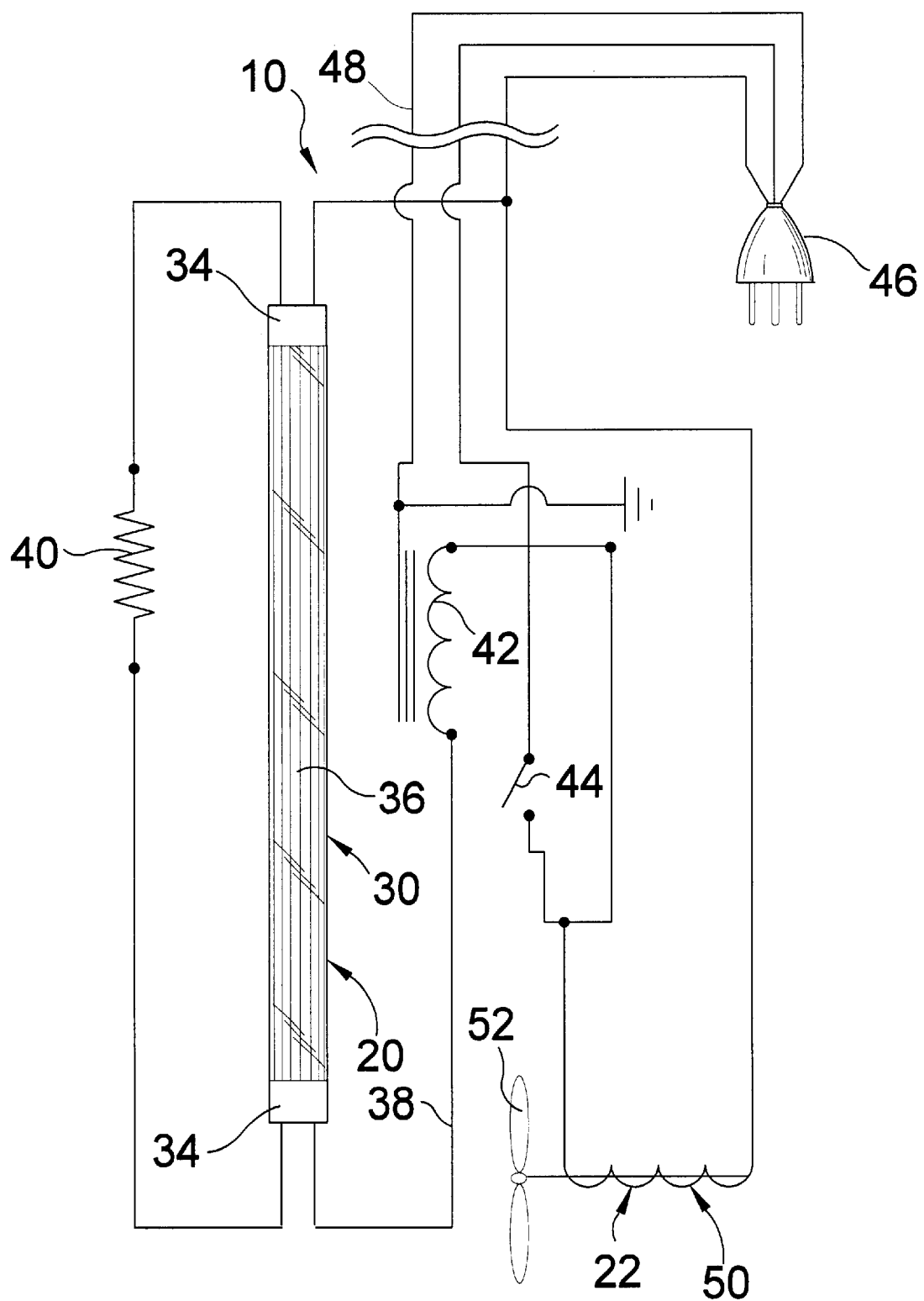
FIG. 3 is a schematic diagram of the electrical circuitry thereof.

Turning now descriptively to the drawings, in which similar reference characters denote similar elements throughout the several views, FIGS. 1 through 3 illustrate an air purifier indicated generally by the numeral 10.

The air purifier 10 of the present invention is illustrated in FIG. 1 positioned within a room 11 of a structure and sculpted so as to blend in with the decor of the room 11. The air purifier 10 has a housing 12 forming the shape of a stand for retaining items such as a plant, flower pot 66 or other ornamental object thereon and is designed to sit securely on a flat horizontal surface such as the floor 18 of the room 11. The housing 12 includes a plurality of air inlet ports 14 positioned on a bottom side 15 thereof and a plurality of air outlet ports 16 positioned on a top side 17 thereof Each air inlet port 14 includes a screen 56 positioned thereover, to help stop large particles in the dust from entering the housing 12. The bottom side 15 of the housing 12 forms a base 28 and the top side 17 has a flat top surface 64 thereon. The base 28 and the flat top surface 64 are connected together by an elongated midsection 26 forming a cabinet therein. An air purifying system is retained within the midsection 26 as will be described herein with reference to FIGS. 2 and 3. The air purifying system communicates with the ambient atmosphere via the air inlet port 14 on the base side 15 and air outlet ports 16 on the top side 17 of the housing 12.

While a preferred structure and shape for the housing 12 is shown and described herein, those of ordinary skill in the art who have read this description will appreciate that there are numerous other structures and shapes for the housing 12 and, therefore, as used herein the phrase "means for retaining the air purifying system therein" should be construed as including all such structures as long as they achieve the desired result of retaining the air purifying system therein, and therefore, that all such alternative mechanisms are to be considered as equivalent to the one described herein.

A switch 44 is positioned to extend from a side of the elongated cabinet 26 for turning the air purifier 10 between an "ON" state and an "OFF" state. When the switch 44 turns the air purifier 10 on, the air purifying system causes air to be drawn in to the housing 12 through the air inlet ports 14. The air drawn through the air inlet ports 14 travels through the elongated cabinet 26, past the air purifying system and back to the atmosphere surrounding the air purifier 10 through the air outlet ports 16. A viewing lens 60 is also provided in the elongated cabinet 26 to allow a person to see the air purifying system and thereby indicate that the air purifier 10 is on and the air purifying system is operating. The viewing lens 60 is able to sufficiently deflect ultraviolet rays generated by the air purifying system so as to not affect or injure the eyes of a person looking thereat.

A facility 20 within the housing 12, is for producing ultraviolet rays and ozone as shown in FIGS. 2 and 3. A component 22 within the housing 12 between the facility 20 and the air inlet ports 14, is for drawing air in through the air inlet ports 14 and directing the air towards the facility 20. Extending from the component 22 and through the elongated cabinet 26 is a passageway 70. The passageway 70 encircles the facility 20 and extends to the top side 17 of the housing 12.

The housing 12 includes the elongated enclosed cabinet 26 positioned between and connecting the base 28 and the top side 17 of the air purifier. The elongated enclosed cabinet 26 supports the ultraviolet ray producing facility 20 therein. The hollow base member 28 has the air inlet ports 14 extending through a side thereof The hollow base member 28 supports the elongated enclosed cabinet 26 in an upright position, and includes the first filter element therein for capturing and retaining particles within the air drawn through the air inlet ports. The air drawing component 22 is held by the hollow base member directly below the ultraviolet ray producing facility 20. The first filter element 24 includes a high efficiency filter pad 54 and is positioned within the base 28 of the housing 12 between the air inlet ports 14 and the air drawing component 22 for trapping small particles, such as pollen and dust, from the air drawn through the air inlet ports 14. The base 15 also contains a bottom access opening 68, as shown in FIG. 2. The access opening 68 allows for the high efficiency filter pad 54 to be removed and replaced when needed by simply lifting the housing off of the floor 18.

The passageway 70 is positioned to extend through the elongated enclosed cabinet 26 on a side of the air drawing component opposite the first filter element 24 for receiving air drawn through the first filter element 24. The passageway 70 encircles the facility 20 completely and allows the air drawn therethrough to be exposed to ultraviolet rays produced by the facility 20 on all sides of the facility 20. Thus, the path of the air through the elongated enclosed cabinet 26 is extended to a maximum possible distance allowing for longer exposure to the ultraviolet rays and ozone to enhance the filtering of the air. A removable back panel 62 is also provided on the elongated enclosed cabinet 26. When the back panel 62 is removed, the ultraviolet ray tube 36 can be removed and replaced when needed. The path traveled by air drawn into the air purifier 10 is illustrated in FIG. 2 by the arrows extending therethrough in the form of a line.

The top side 17 is positioned at a side of the passageway 70 opposite the base 15 for receiving the air passing through the passageway 70. The top side 17 includes the air outlet ports 16 providing a passage for filtered and purified air to return to the outside of the air purifier 10. An optional second filter element 74 is shown positioned in the top side 17 between the second air drawing component and the air outlet ports 16 for further filtering the air passing through the air outlet ports 16. The second filter 74 may be scented for freshening and providing an odor to the air as it passes therethrough. The scented filter 74 provides a form of aroma therapy by scenting the air with a desired odor. Odors which the air may be scented include but are not limited to popourri, cherry, strawberry, lemon, pine, peppermint, vanilla, etc. The ultraviolet rays being produced kill bacteria, germs and viruses in the air drawn through the housing 12, while at the same time the ozone being produced will neutralize undesirable odors, such as stale tobacco smoke and mildew in the air drawn through the housing 12. When a scented filter 74 is positioned in the top side 17 to further filter the air, the air exiting through the air outlet ports 17 will not only be clean but also fresh scented. The housing 12 further includes a flat top plate 64 mounted on the cabinet 26 above the air outlet ports 16. The top flat plate is removably connected to the elongated enclosed cabinet 26 for allowing the second filter element 74 to be removed.

The ultraviolet ray producing facility 20 is an ultraviolet lamp assembly 30. The ultraviolet lamp assembly 30 consists of an elongated chassis 32 mounted vertically within the housing 12. A lamp holder 34 is positioned within the chassis 32, while an ultraviolet ray tube 36 is held within the lamp holder 34. The ultraviolet ray producing facility 20 is also able to produce ozone for further purifying the air. The lamp assembly 32 and holder 34 is positioned within a central region of the passageway 70. This allows the air drawn through the passageway 70 to flow around the lamp assembly 30 and be irradiated by the ultraviolet rays produced thereby at all points along its travel through the passageway 70. The chassis 32 has an aperture 58 located adjacent the ultraviolet ray tube 36. The viewing lens 60 being a blue/green borosilicate glass is carried in the housing 12 in front of the aperture 58 of the chassis 32. This allows a person to look safely through the viewing lens 60, to determine if the ultraviolet ray tube 36 is operating when the switch 44 is turned on.

The electric circuit 38 for powering the air drawing component 22 and the ultraviolet ray producing facility 20 is shown in FIG. 3. A starter 40 is electrically connected via the electric circuit 38 to the lamp holder 34. A ballast 42 is electrically connected via the electric circuit 38 to the lamp holder 34. A switch 44 on the housing 12 is electrically connected via the electric circuit 38, between the ballast 42 and the air drawing component 22. A plug 46 on an electric cord 48 is electrically connected to the electric circuit 38, to engage with a wall socket to receive electricity therefrom. The air drawing component 22 is a blower 50 being a motorized fan 52, for forcing the air through the housing 12. The air drawing component 22 is connected to receive electricity from the wall socket through the plug 46.

The operation of the air purifier 10 will now be described with reference to the figures. In operation, the air purifier 10 is first assembled by placing the first and second filter elements 22 and 74 in position in the base and top sides 15 and 17 respectively. The air purifier 10 is then positioned at a desired location in a room 11 and the plug 46 is connected to a wall outlet. The air purifier 10 is now ready for operation.

In order to turn the air purifier 10 ON, the button 44 positioned on the front side of the elongated enclosed cabinet 236 is activated. Activation of this button 44 will cause the ultraviolet lamp assembly 30 to turn on and begin generating ultraviolet rays and ozone. The air drawing component 22 is also be turned on to draw air into the housing.

The air drawing component 22 will draw air through the air inlet ports 14 and through the first filter element 24. The first filter element 24 will act to remove large particles from the air. The size of particles removed from the air is dependent upon the coarseness of the filter used. A very fine filter will act to remove particles of smaller size while a coarse filter will remove particles of a larger size. The air drawn through the first filter element 24 will then be directed to the passageway 70. The passageway provides a path for the air to travel through the elongated enclosed cabinet 26.

The passageway 70 forms a path along and around the ultraviolet lamp assembly 30 along which the air travels. As the air passes through the passageway 70, it is irradiated by the ultraviolet rays produce by the ultraviolet lamp assembly 30 and thus filtered. The passageway 70 extends the distance the air must travel through the elongated enclosed cabinet 26 and thus increases the exposure time of the air to the ultraviolet rays and ozone thereby more effectively filtering the air. The ultraviolet rays being produced kill bacteria, germs and viruses in the air drawn through the housing 12, while at the same time the ozone being produced will neutralize undesirable odors, such as stale tobacco smoke and mildew in the air drawn through the housing 12.

Once through the passageway 70, the air is passed through a second filter element 74. The second filter element 74 may be scented for freshening and providing an odor to the air as it passes therethrough. The scented filter 74 will provide a form of aroma therapy by scenting the air with a desired odor. Odors which the air may be scented include but are not limited to popourri, cherry, strawberry, lemon, pine, peppermint, vanilla, etc. When the scented filter 74 is positioned in the tip side 17 to further filter the air, the air exiting through the air outlet ports 17 will not only be clean but also fresh scented, The fresh scented and filtered air is then provided to the outside of the air purifier through the air outlet ports 16. The air drawn into the air purifier 10 follows the path indicated by the arrows shown in FIG. 2. The path followed by the arrows illustrates the air passing through the air inlet ports 14 and first filter element 24 to the passageway 70. The air then passes along the path created by the passageway 70 to the top side 17 where the air passes through the second filter element 74 and through the air outlet ports 16 to the ambient atmosphere. Thus, the air in a room occupied by the air purifier 10 is able to be cleaned, filtered and scented.

From the above description it can be seen that the air purifier of the present invention is able to overcome the shortcomings of prior art devices by providing an air purifier which is able to disinfect the air in the surrounding atmosphere, particularly in a sick-bay, to reduce the spread of infectious disease and emits ozone, a powerful oxidizing agent, for neutralizing undesirable odors, such as stale tobacco smoke and mildew. The air purifier includes a passageway extending therethrough and surrounding the source of ozone and ultraviolet light through which air entering the purifier will flow in order to expose air drawn therein to the ozone and ultraviolet rays for a maximum possible amount of time. The air purifier also includes filters positioned at least at the inlet port and optionally at the outlet port for further purifying the air and a component for drawing into the air purifier at the input port. Furthermore, the air purifier of the present invention is simple and easy to use and economical in cost to manufacture.

It will be understood that each of the elements described above, or two or more together may also find a useful application in other types of methods differing from the type described above.

While certain novel features of this invention have been shown and described are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A device for purifying air within a room, said device consisting of:
   a) a housing having a plurality of air inlet ports and a plurality of air outlet ports, said housing including a hollow base member having said air inlet ports positioned thereon, a top side and an elongated cabinet connecting said base and said top side with said top side overhanging said cabinet, with said air outlet ports located in said elongated cabinet adjacent to and below the overhanging top side, each of said air inlet ports having a polyester screen for aiding in preventing large particles in the air from entering said housing;
   b) means for generating ultraviolet rays and ozone positioned within said housing;
   c) means for drawing air into said housing through said air inlet ports being a motorized blower for forcing air through said housing;
   d) a passageway leading from said air inlet ports and encircling said generating means to said air outlet ports providing a path for air drawn into said housing by said drawing means, the air making a single pass by and around said generating means, whereby the ultraviolet rays produced by said generating means purify the air passing thereby through said passageway, while ozone produced by the generating means neutralizes undesirable odors in the air drawn through said housing, said passageway maximizing a distance traveled by the air through said housing and exposure of the air to said ultraviolet rays and ozone;
   e) a first filter element being a high efficiency filter pad and positioned within said base between said air drawing means and said air inlet ports for trapping small particles within the air drawn through said air inlet ports, said first filter element filter pad being planar in shape and oriented at an isosceles angle to the horizontal so that air entering the inlet ports pass through the inlet filter pad and turn upwardly;
   f) said generating means being a single ultraviolet lamp assembly comprising an elongated chassis mounted vertically within said housing, a lamp holder positioned in said chassis, an ultraviolet ray tube positioned in said lamp holder, an electric circuit, a starter electrically connected via said electric circuit to said lamp holder, a ballast electrically connected via said electric circuit to said lamp holder, a switch on said housing electrically connected via said electric circuit between said ballast and said air drawing means, and a plug on an electric cord electrically connected to said electric circuit to engage with a wall socket to receive electricity therefrom;

g) a second filter element positioned in said housing adjacent said top side member between said passageway and said outlet ports for further filtering air which has passed through said passageway, said second filter element being planar and oriented at an isosceles angle with respect to the horizontal so that air passing through said second filter element makes a right angle turn to exit through said outlet ports, and said second filter element being scented for providing a desired scent to air passing therethrough, the scent being one of potpourri, cherry, strawberry, lemon, lime, peppermint and vanilla;

h) said housing having an aperture located adjacent said ultraviolet ray tube and further including a viewing lens of blue/green borosilicate glass positioned to cover said aperture and thereby allow a person to look safely therethrough to determine if said ultraviolet ray tube is operating when said switch is turned on, a removable back panel for selectively replacing said ultraviolet ray tube, said top side having a flat top plate for retaining articles placed thereupon, and said base further including a bottom access opening for selectively replacing said high efficiency filter pad.

* * * * *